United States Patent [19]
Deckman et al.

[11] Patent Number: 5,942,119
[45] Date of Patent: *Aug. 24, 1999

[54] SEPARATION PROCESS USING ZEOLITE MEMBRANE

[75] Inventors: Harry William Deckman, Clinton, N.J.; Edward William Corcoran, Jr., Easton, Pa.; Lothar R. Czarnetzki, Leiderdorp, Netherlands; James Alexander McHenry, Washington, N.J.

[73] Assignee: Exxon Research and Engineering Company, Florham Park, N.J.

[*] Notice: This patent is subject to a terminal disclaimer.

[21] Appl. No.: 08/789,586

[22] Filed: Jan. 24, 1997

Related U.S. Application Data

[63] Continuation-in-part of application No. 08/591,819, Jan. 25, 1996, abandoned.

[51] Int. Cl.⁶ ..................................................... B01D 61/00
[52] U.S. Cl. .............................. 210/651; 210/653; 95/45; 95/50; 95/55; 585/481
[58] Field of Search ..................................... 210/651, 640, 210/653, 500.25, 650; 95/45, 50, 55; 585/481

[56] References Cited

U.S. PATENT DOCUMENTS

| | | | |
|---|---|---|---|
| 4,163,028 | 7/1979 | Tabak et al. | 585/481 |
| 4,699,892 | 10/1987 | Suzuki | 502/60 |
| 4,925,459 | 5/1990 | Rojey et al. | |
| 5,104,425 | 4/1992 | Rao et al. | |
| 5,110,478 | 5/1992 | Haag et al. | |
| 5,209,838 | 5/1993 | Sleppy et al. | |
| 5,332,424 | 7/1994 | Rao et al. | |
| 5,354,547 | 10/1994 | Rao et al. | |
| 5,362,522 | 11/1994 | Barri et al. | 427/435 |
| 5,435,836 | 7/1995 | Annand et al. | |
| 5,507,856 | 4/1996 | Rao et al. | |
| 5,516,956 | 5/1996 | Abichandani et al. | |
| 5,716,527 | 2/1998 | Deckman et al. | 210/651 |

FOREIGN PATENT DOCUMENTS 1235684 4/1988 Canada.

*Primary Examiner*—Ana Fortuna
*Attorney, Agent, or Firm*—Paul E. Purwin

[57] ABSTRACT

The present invention is an improvement in a separation process. When molecular sieve membranes are used in a separation process transport flux decays over time. It has been discovered that the presence of hydrogen in the feed stream, permeate stream, or feed stream when present, either alone or in combination, causes a reduction in flux decay.

7 Claims, No Drawings

SEPARATION PROCESS USING ZEOLITE MEMBRANE

This application is a continuation in part of application Ser. No. 08/591,819, filed Jan. 25, 1996, abandoned.

FIELD OF THE INVENTION

The present invention is directed towards processes using molecular sieve membranes and molecular sieve membrane composites. More specifically, the invention is directed towards a method that reduces membrane flux decay in such processes.

Background of the Invention

Molecular sieve membranes and molecular sieve membrane composites can be used in molecular separation processes. In these processes, a feed stream containing at least two different molecular types is fed to one side of a membrane and at least one molecular species called permeate is transported through the membrane to the opposite side. Feed stream molecules that are not transported through the membrane are called retentate molecules. Frequently an additional molecular stream called a sweep stream removes the permeate from the side of the membrane that is not in contact with the feedstream. The membrane is therefore situated as a barrier between two regions: one region is in contact with the membrane and the feed stream; the second region is in contact with permeate molecules and an optional sweep stream.

The rate at which permeate is transported through an area of the membrane is called the transport flux. Transport flux increases with process temperature. High transport flux, which increases permeate yield, is a desirable property. Unfortunately, transport flux decreases over time with a more rapid decrease at elevated temperatures. Consequently there is a need to at least reduce, if not substantially prevent, transport flux decay.

SUMMARY OF THE INVENTION

Briefly stated, the present invention is based on the discovery that transport flux decay can be reduced by conducting the separation process in the presence of hydrogen. Thus, in one embodiment of the invention, a molecular sieve membrane used in a separation process is contacted with sufficient hydrogen at the process temperature to reduce transport flux decay. In a preferred embodiment, hydrogen is added to at least one of the feed stream or permeate stream in an amount sufficient to prevent substantially transport flux decay. Hydrogen can be added during the separation process. Alternatively, hydrogen can be added from time to time to restore transport flux to an earlier higher value. Hydrogen may also be used to restore membrane transport flux to an earlier higher value during periods of time in which the feed stream, permeate stream, or sweep stream when present is diverted away from the membrane.

Detailed Description

Molecular sieve membranes can be used in separation processes and catalyzed processes. Molecular sieve membranes can also be used in processes where both separation and catalysis occur; these process are called catalytic membrane reactions. The membranes can be free standing or supported, and can also be one component of a molecular sieve membrane composite. Permselective molecular sieve membranes are typically used in separation processes and catalytic membrane reactions. Permselective molecular sieve membranes selectively transport at least one molecule of the feedstream across the membrane. Of the molecular sieve materials used in molecular sieve membranes, zeolites are preferred.

Molecular sieve membranes and molecular sieve membrane composites are known in the art. Often these terms are used interchangeably. For the purposes of this invention, the terms molecular sieve membrane and molecular sieve membrane composite are used according to the language of reference PCT/US95/08513.

The present invention can be practiced with molecular sieve membrane and molecular sieve membrane composites that include a porous support material. Additionally, the invention can be practiced when an optional growth enhancing layer or seeding layer is included between the molecular sieve membrane and the support. The invention can also be practiced in cases where non selective permeation paths are present and a reparation coating is applied and when optional selectivity enhancing coatings are applied. When a molecular sieve membrane is used in combination with an optional support, growth enhancing or seeding layer, reparation coating, or growth enhancing layer, the combination is referred to as a composite or a molecular sieve membrane composite.

References disclose the use of molecular sieve membranes and molecular sieve membrane composites as separators and as components of catalytic membrane reactors. Therefore it was greatly surprising that during the use of molecular sieve membranes and molecular sieve membrane composites as separators or as components of catalytic membrane reactors the flux of permeate through the membrane was observed to decrease with time. No reference disclosed or suggested the observed decrease in membrane flux.

It has been discovered that operating molecular sieve membranes and molecular sieve membrane composites in the presence of hydrogen substantially reduces flux decay. Stated differently, it has been discovered that in separation processes an amount of hydrogen can be added in order to maintain transport flux at a predetermined acceptable level. Flux decay reduction is achieved when hydrogen is present in the feed stream, the permeate, or the optional sweep stream when present, or in any combination of feed stream, permeate, and optional sweep stream. When molecular sieve membranes and molecular sieve membrane composites are operated without the presence of hydrogen while using a hydrocarbon or oxygenated feed, the flux through the membrane is observed to decay in an approximately exponential fashion with time.

In the absence of hydrogen, permeate flux, F, through the molecular sieve membrane at any particular time, t, can be approximately determined from the flux at some arbitrary earlier time, $F_0$ by the use of a rate constant, K, according to the following relationship:

$$F = F_0 e^{-Kt}$$

The units of flux used herein are Kg/M²-day. This relationship describes an exponential decay of flux with time. Using this relationship, a lifetime for the flux, $\tau$, can be defined as the length of time for the permeate flux to decay to 1/e of its original value. $\tau$ can be calculated from the relationship $$\tau = 1/K$$

Similarly, a flux half life, $t_{1/2}$, is defined as the time in which the initial flux decays to half its original value. The half life is determined from the relationship $$\tau_{1/2} = \tau(\ln \tfrac{1}{2})$$

The rate of flux decay, K, increases with operating temperature and depends on the molecular composition of the feed stock and membrane composition. This approximately exponential decay of flux with time is especially troublesome during high temperature separation processes with hydrocarbon feeds. It is especially advantageous to operate the separation process at high temperatures because the diffusion coefficients of typical permeates increases with temperature. Additionally, in the case of membranes used as components in a catalytic membrane reactor, high temperatures may be required because many catalytic processes operate only at high temperatures. However, the half life for the flux decreases dramatically as the operating temperature is increased.

An example where transport flux reduction would be especially troublesome is the separation of paraxylene permeate from a feed stream comprising a mixture of xylenes and ethylbenzene. Transport flux decay would quickly reduce paraxylene yield in the preferred separation temperature range of 170° C. to 500° C., and flux decay has been routinely observed with permselective molecular sieve membranes and molecular sieve membrane composites fabricated on alumina and steel supports. MFI zeolite membranes and MFI zeolite membrane composites that were permselective for paraxylene were found to have a flux half life at 225° C. of 10 to 10000 times less than at room temperature when operated with an argon sweep removing the paraxylene permeate from a mixed A8 aromatic feed. However, while separating xylenes at 300° C., first with an inert sweep gas such as argon or nitrogen and then adding hydrogen to the sweep, transport flux was increased and remained stable when hydrogen was present, whereas it decayed when hydrogen was absent.

While the flux decay prevention and remediation through the presence of hydrogen can be observed in all cases where the feedstream is derived from hydrocarbons and oxygenates, the rate of change of transport flux in time depends on separation and separation/catalysis process conditions such as temperature, pressure, trans-membrane pressure, and space velocity. The rate of change also will depend on feed composition, membrane and membrane composite composition and structure, hydrogen partial pressure, the ratio of the amount of hydrogen present to the amount of feed, and other similar parameters.

The exact rate of flux decay varies with choice of membrane and also increased slightly with feed pressure. Feed pressure of the mixed A8 aromatic feed (xylenes and ethylbenzene) varied from 1 atmosphere to 15 atmospheres in these experiments and sweep pressure was maintained equal to or 2 to 10 atmospheres below the feed pressure. At temperatures approaching ~400° C. the half life of the flux was in general less than ~2 days when hydrogen was not present during paraxylene separations. This rapid rate of flux decay is a problem for any practical higher temperature application of molecular sieve membranes. Higher temperature operation is desirable because permselective transport increases with temperature. For example, in a preferred embodiment such as paraxylene separation the invention is practiced at temperatures above 225° C. and preferably at temperatures above 300° C.

Reductions in flux decay occur when the separation is conducted in the presence of hydrogen in an amount of at least about 0.1 mole percent of the total molecules in the feed and sweep. At temperatures greater than 225° C. at least 1 mole percent hydrogen must be present, although further reductions in flux decay will be observed when there is at least 10 mole percent hydrogen in the total number of molecules in the feed and sweep. At temperatures greater than 300° at least 20 mole percent hydrogen should be in the total number of molecules in the feed and sweep although further reductions in flux decay will be observed when about 30 to about 60 mole percent hydrogen is present.

The addition of hydrogen to separation and combinations of separation and catalytic reactions reduces flux decay in cases where hydrogen is not present in sufficient quantity initially. Hydrogen can be added to either the feed or sweep if one is employed in the process. However, it should be noted that hydrogen readily diffuses through molecular sieve membranes, and therefore contacts both faces of the molecular sieve membrane regardless of whether it is introduced on the feed stream or permeate side of the membrane.

Separations and combinations of separation and catalytic processes involving hydrocarbon feed stocks benefit from the invention. Among these are separating normal alkanes from co-boiling hydrocarbons especially n-C10 to n-C16 alkanes from kerosene, separating normal alkanes and alkenes from the corresponding branched alkane and alkene isomers, separating aromatic compounds from one another especially separating C8 aromatic isomers from each other and more especially paraxylene from a mixture of xylenes and optionally ethylbenzene, separating aromatics of different carbon numbers such as mixtures of benzene, toluene, and mixed C8 aromatics, separating aromatic compounds from aliphatic compounds especially aromatic molecules with from 6 to 8 carbon atoms from C5 to C10 (naphtha range) aliphatics, and separating olefinic compounds from saturated compounds, especially light alkenes from alkane/alkene mixtures especially ethene from ethane and propene from propane.

Separations and combinations of separation and catalytic processes involving oxygenated feed stocks benefit from the invention. Among these are separating alcohols from other hydrocarbons especially alkanes and alkenes that may be present in mixtures formed during the manufacture of the alcohols. These processes can be performed by contacting a flowing mixture with one face of the molecular sieve membrane so that at least one component of the mixture has a different steady state permeability through the molecular sieve membrane from the other components and recovering the more rapidly permeating component or components from the other face of the molecular sieve membrane. Hydrogen should be present in either the feed or the optional sweep.

The invention also provides a method for improving a process for catalyzing a chemical reaction. These processes involve contacting a feed stock with one face of a molecular sieve membrane or molecular sieve membrane composite that is in active catalytic form and operating under catalytic conversion conditions, and then recovering at least one conversion product from an opposite face of the membrane, advantageously in a concentration differing from its equilibrium concentration in the reaction mixture. These processes include recovering a paraxylene rich mixture from the reactor or reactor product in a xylenes isomerization process and aromatic compounds from aliphatics. The improvement is the reduction in membrane flux decay that occurs when the processes are conducted in the presence of a sufficient amount of hydrogen in either the feed stream or product stream.

Still further benefits can be obtained in catalyzing chemical reactions when one reactant of a reaction contacts one face of a molecular sieve membrane in active catalytic form and under catalytic conversion conditions while controlling the addition of a second reactant by diffusion from the opposite face of the membrane in order to more precisely control reaction conditions. The improvement comprises the presence of hydrogen in either the reactant or product streams so as to maintain membrane activity. Examples include controlling ethylene, propylene or hydrogen addition to benzene in the formation of ethylbenzene, cumene or cyclohexane respectively.

Additionally, the invention can be practiced in cases where catalytic functions are incorporated into the membranes or membrane composites themselves. Some of the locations in the membrane or membrane composite where the catalytic function can be incorporated include within the molecular sieve layer and within the porous support. The invention can be practiced when the catalytic function is localized as in these and similar cases, as well as when the catalytic function is distributed throughout all or some of the layers of the membrane or membrane composite. The invention can be practiced when the membrane or membrane composite is impregnated with catalytically active metals such as Pt that can impart the catalytic function to the membrane. In addition, the invention can be practiced when the catalytic function is incorporated into a membrane reactor by locating conventional catalyst particles near one or more surfaces of the membrane such that specific reaction products or reactants are continuously and selectively removed or added to the reaction zone throughout the reactor. The invention can be practiced regardless of the spatial relationship of the catalyst to the membrane. For example, the invention can be practiced when the catalyst is located on or near either the permeate or retentate side of the membrane or membrane composite. Processes using these arrangements can be improved through the presence of hydrogen in the feed stream, reactant stream, product stream alone or in combination with one another. The hydrogen results in a reduction in the rate of decrease of membrane activity.

EXAMPLE

A molecular sieve membrane was utilized to separate paraxylene from a mixture comprising para, ortho, and meta xylene at 360° C. and ambient pressure. Hydrogen was present in the hydrocarbon stream, and the molar ratio of hydrocarbon to hydrogen was 1:1. Additionally, the membrane's permeate side was continuously purged with hydrogen. The total hydrocarbon flux through the membrane was 2.4 Kg/m$^2$day.

The separation was then conducted with the same membrane in the absence of hydrogen, and the total hydrocarbon flux through the membrane dropped to 0.9 kg/m$^2$.

The membrane was then exposed to a pure hydrogen purge at 450° C. and ambient pressure. After 30 hr of this hydrogen treatment, the separation was conducted again and the hydrocarbon flux across the membrane was measured to have increased to 3.0 kg/m$^2$day.

What is claimed is:

1. An improvement in a separation process in which (a) a feed stream containing at least two different molecular types selected from the group consisting of hydrocarbons, oxygenates, and mixtures thereof is fed to a first face of a molecular sieve membrane composite having a porous support, a molecular sieve membrane, and a growth enhancing layer situated therebetween and (b) a permeate stream is removed is removed at a second face of the membrane composite, the improvement comprising:

conducting the process with hydrogen present in at least one of the feed stream and permeate stream.

2. The improvement of claim 1 wherein the hydrogen is added to at least one of the feed stream and permeate stream.

3. The improvement of claim 1 wherein the hydrogen is added to the feed stream.

4. The improvement of claim 1 wherein the hydrogen is present in a concentration of about 0.1 mole percent of the feed stream to about 60 mole percent of the feed stream.

5. The improvement of claim 1 wherein the separation process occurs in a temperature range of about 170° C. to about 300° C.

6. The improvement of claim 1 wherein the permeate stream contains paraxylene.

7. The improvement of claim 1 wherein the hydrogen is added to the permeate.

* * * * *